United States Patent
Okaguchi

(10) Patent No.: US 12,378,955 B2
(45) Date of Patent: Aug. 5, 2025

(54) FLUID CONTROL DEVICE AND OUTPUT ADJUSTMENT METHOD

(71) Applicant: Murata Manufacturing Co., Ltd., Kyoto (JP)

(72) Inventor: Kenjiro Okaguchi, Kyoto (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 63 days.

(21) Appl. No.: 18/476,899

(22) Filed: Sep. 28, 2023

(65) Prior Publication Data
US 2024/0018956 A1 Jan. 18, 2024

Related U.S. Application Data

(63) Continuation of application No. PCT/JP2022/007852, filed on Feb. 25, 2022.

(30) Foreign Application Priority Data

Apr. 1, 2021 (JP) .................................. 2021-062757

(51) Int. Cl.
*F04B 49/06* (2006.01)
*A61M 11/00* (2006.01)
(Continued)

(52) U.S. Cl.
CPC ............. *F04B 49/06* (2013.01); *A61M 11/00* (2013.01); *F04B 23/04* (2013.01); *F04B 43/046* (2013.01)

(58) Field of Classification Search
CPC ........ F04B 23/04; F04B 49/06; F04B 43/046; A61M 11/00
See application file for complete search history.

(56) References Cited

U.S. PATENT DOCUMENTS

2005/0163623 A1  7/2005  Okada
2011/0015738 A1* 1/2011  Vaingast ............... A61F 2/004
                                              623/14.13
(Continued)

FOREIGN PATENT DOCUMENTS

JP   2005-207368 A   8/2005
WO   2018/198288 A1  11/2018
(Continued)

OTHER PUBLICATIONS

English Translation of WO-2019202831-A1 obtained Jan. 14, 2025 (Year: 2019).*

(Continued)

*Primary Examiner* — Connor J Tremarche
(74) *Attorney, Agent, or Firm* — McDonald Hopkins LLC

(57) ABSTRACT

The present disclosure provides a fluid control device and an output adjustment method with which the output of a pump can be easily adjusted even if an atmospheric pressure changes. A pump unit includes a first flow path, a u piezoelectric pump, a d piezoelectric pump, a second flow path, a third flow path, a control circuit capable of controlling driving of the u piezoelectric pump and the d piezoelectric pump, and a current sensor for detecting respective currents of the u piezoelectric pump and the d piezoelectric pump. The control circuit is capable of adjusting at least one of the output of the u piezoelectric pump and the output of the d piezoelectric pump on the basis of a difference (Iu−Id) between a current Iu of the u piezoelectric pump and a current Id of the d piezoelectric pump detected by the current sensor.

8 Claims, 5 Drawing Sheets

(51) Int. Cl.
*F04B 23/04* (2006.01)
*F04B 43/04* (2006.01)

(56) References Cited

U.S. PATENT DOCUMENTS

| | | | |
|---|---|---|---|
| 2012/0265125 A1* | 10/2012 | Kawamura | A61M 5/145 |
| | | | 604/67 |
| 2015/0174910 A1* | 6/2015 | Kaneko | B41J 2/17596 |
| | | | 347/85 |
| 2020/0141415 A1* | 5/2020 | Tamai | F16C 32/048 |
| 2020/0378380 A1 | 12/2020 | Okaguchi | |
| 2021/0404461 A1 | 12/2021 | Okaguchi | |
| 2022/0403835 A1 | 12/2022 | Okaguchi et al. | |

FOREIGN PATENT DOCUMENTS

| | | | | |
|---|---|---|---|---|
| WO | 2019/198305 A1 | | 10/2019 | |
| WO | WO-2019202831 A1 | * | 10/2019 | F04B 17/003 |
| WO | 2020/217934 A1 | | 10/2020 | |
| WO | 2021/171729 A1 | | 9/2021 | |

OTHER PUBLICATIONS

International Search Report for PCT/JP2022/007852 dated May 10, 2022.

* cited by examiner

FIG. 4A
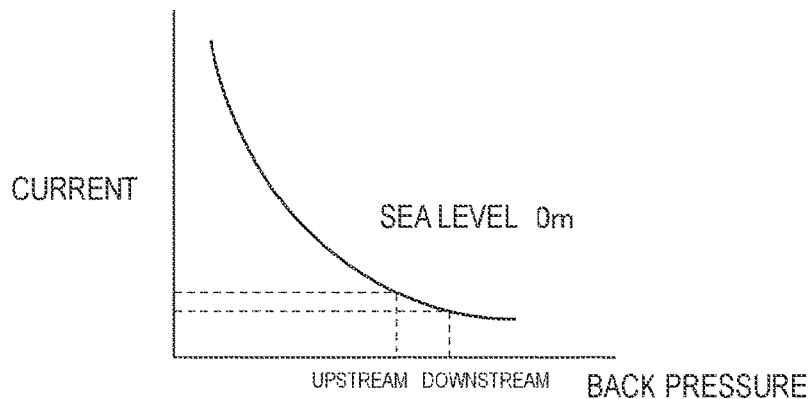
FIG. 4B
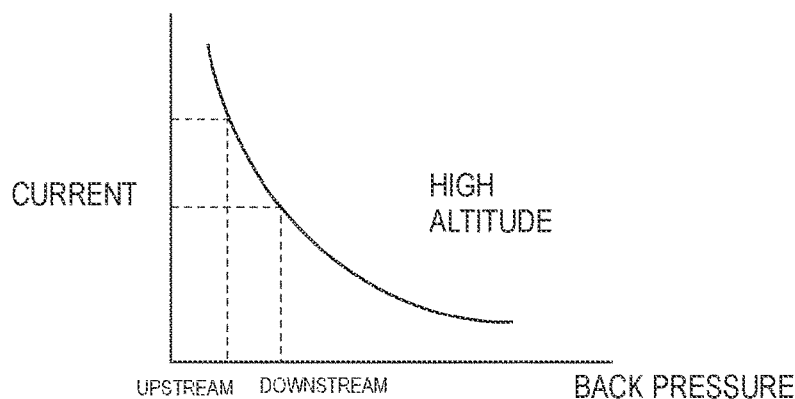
FIG. 5
| SEA LEVEL | Iu-Id | ADJUSTMENT AMOUNT (u) | ADJUSTMENT AMOUNT (d) | ATMOSPHERIC PRESSURE (hPa) |
|---|---|---|---|---|
| 0m | $\alpha$ | 0% | 0% | 1013 |
| ⋮ | ⋮ | ⋮ | ⋮ | ⋮ |
| 500m | $\beta\,(>\alpha)$ | 0% | 0% | 957 |
| ⋮ | ⋮ | ⋮ | ⋮ | ⋮ |
| 1000m | $\gamma\,(>\beta)$ | +20% | +20% | 903 |
| ⋮ | ⋮ | ⋮ | ⋮ | ⋮ |
| 3000m | $\delta\,(>\gamma)$ | −30% | 0% | 711 |
| ⋮ | ⋮ | ⋮ | ⋮ | ⋮ |

FLUID CONTROL DEVICE AND OUTPUT ADJUSTMENT METHOD

CROSS REFERENCE TO RELATED APPLICATION

This is a continuation of International Application No. PCT/JP2022/007852 filed on Feb. 25, 2022 which claims priority from Japanese Patent Application No. 2021-062757 filed on Apr. 1, 2021. The contents of these applications are incorporated herein by reference in their entireties.

BACKGROUND OF THE DISCLOSURE

Field of the Disclosure

The present disclosure relates to a fluid control device and an output adjustment method.

Description of the Related Art

Fluid control devices each including a pump and a control circuit have been developed. International Publication No. 2019/198305 (Patent Document 1) discloses that a plurality of pumps are connected in series for the improvement of performance and an output such as a pressure or a flow rate. Specifically, in a fluid control device in which two pumps are connected in series, a first pump and a second pump are connected in series.
Patent Document 1: International Publication No. 2019/198305

BRIEF SUMMARY OF THE DISCLOSURE

A fluid control device in which two pumps are connected in series can improve an output as compared with a fluid control device using a single pump. However, if a fluid control device in which two pumps are connected in series is used at a place with a low atmospheric pressure, such as a high altitude, the output of the fluid control device decreases. A method of adjusting the output of a pump of a fluid control device using a sensor such as a barometer can be considered, but the need to provide a sensor such as a barometer leads to the increase in a manufacturing cost.

It is a possible benefit of the present disclosure to provide a fluid control device and an output adjustment method with which the output of a pump can be easily adjusted even when an atmospheric pressure varies.

A fluid control device according to an embodiment of the present disclosure includes a first flow path, a first pump having a first flow inlet connected to one end of the first flow path and a first flow outlet, a second pump having a second flow inlet and a second flow outlet, a second flow path having one end connected to the first flow outlet of the first pump and another end connected to the second flow inlet of the second pump, a third flow path connected to the second flow outlet of the second pump, a control unit capable of controlling driving of the first pump and the second pump, and a detection unit configured to detect an electric quantity of the first pump and an electric quantity of the second pump. The control unit is capable of adjusting at least one of an output of the first pump and an output of the second pump based on a difference in electric quantity between the first pump and the second pump detected by the detection unit.

An output adjustment method according to an embodiment of the present disclosure is a method of adjusting at least one of an output of a first pump and an output of a second pump in a fluid control device including a first flow path, the first pump having a first flow inlet connected to one end of the first flow path and a first flow outlet, the second pump having a second flow inlet and a second flow outlet, a second flow path having one end connected to the first flow outlet of the first pump and another end connected to the second flow inlet of the second pump, a third flow path connected to the second flow outlet of the second pump, a control unit capable of controlling driving of the first pump and the second pump, and a detection unit configured to detect an electric quantity of the first pump and an electric quantity of the second pump. The output adjustment method includes a step of detecting a difference in electric quantity between the first pump and the second pump and a step of adjusting at least one of the output of the first pump and the output of the second pump based on the detected difference in electric quantity between the first pump and the second pump.

According to the present disclosure, at least one of the output of the first pump and the output of the second pump is adjusted on the basis of the detected difference in electric quantity between the first pump and the second pump. Accordingly, even if an atmospheric pressure changes, the output of the pump can be easily adjusted.

BRIEF DESCRIPTION OF THE SEVERAL VIEWS OF THE DRAWINGS

FIG. 5 is a diagram illustrating the contents of a table stored in a storage unit according to an embodiment.

DETAILED DESCRIPTION OF THE DISCLOSURE

Figure 1:
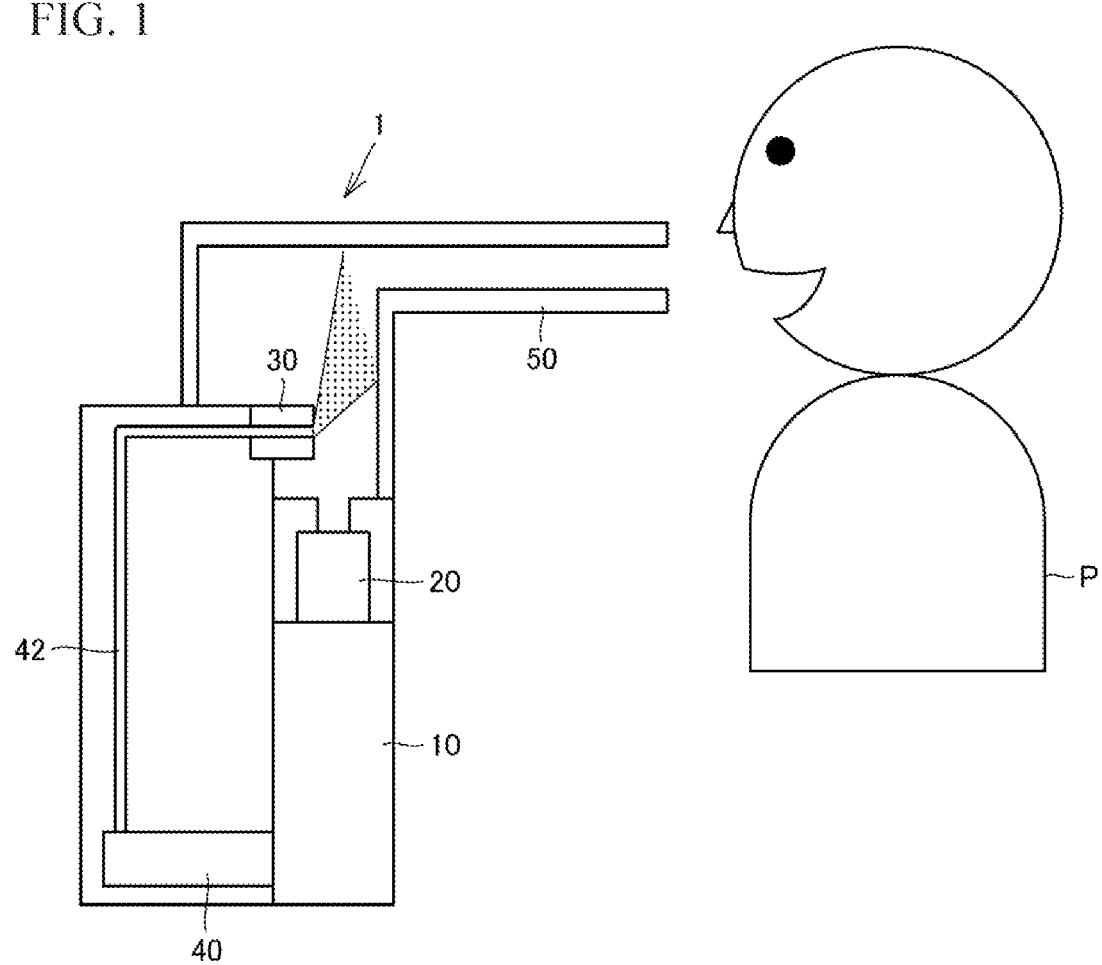
FIG. 1 is a schematic diagram describing the configuration of a nebulizer according to an embodiment.

A fluid control device according to an embodiment will be described in detail below with reference to the drawings. In the drawings, the same reference numeral is used to represent the same part or the corresponding part.

Embodiment

An exemplary case where a pump unit (fluid control device) including two series-connected pumps is used for a nebulizer will be described in the following embodiment. A nebulizer is a device that, for example, an asthmatic patient uses to orally inhale a drug solution, and generates a powerful air flow in the pump unit to atomize a drug solution. A device for which the pump unit is used is not limited to a nebulizer and may be a discharge device such as an aroma diffuser or a humidifier or a suction device such as a nasal aspirator.

FIG. 1 is a schematic diagram describing the configuration of a nebulizer 1 according to an embodiment. The nebulizer 1 includes a pump unit 10, an air nozzle 20, an atomizing nozzle 30, a drug solution tank 40, and a mouthpiece 50. A patient P holds the tip portion of the mouthpiece 50 in the mouth thereof and inhales an atomized drug solution discharged from the tip portion.

The pump unit 10 is a pump for producing compressed air and includes two pumps that are connected in series for the improvement of performance and an output such as a pressure or a flow rate. The pump unit 10 including piezoelectric pumps that are small in size and weight and have excellent quietness will be described, but may include pumps using motors. Although not illustrated, a piezoelectric pump includes a piezoelectric element and a pump chamber in a housing and moves a fluid by varying the volume or pressure of the pump chamber using the displacement of the piezoelectric element caused by driving. The configuration of the pump unit 10 will be described in detail below.

The air nozzle 20 delivers the compressed air produced by the pump unit 10 to the atomizing nozzle 30. A powerful air flow generated by the air nozzle 20 produces a negative pressure at the tip portion of the atomizing nozzle 30, and a drug solution is sucked up from the drug solution tank 40 through a pipe 42. The drug solution sucked up to the tip portion of the atomizing nozzle 30 is atomized by an air flow from the air nozzle 20 and is delivered to the mouth of the patient P through the mouthpiece 50.

Figure 2:
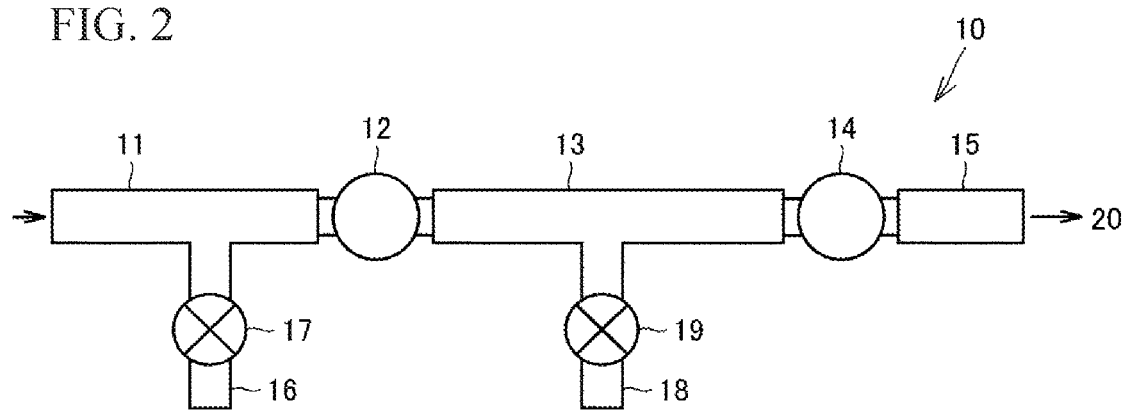
FIG. 2 is a schematic diagram illustrating the configuration of a pump unit according to an embodiment.
Figure 3:
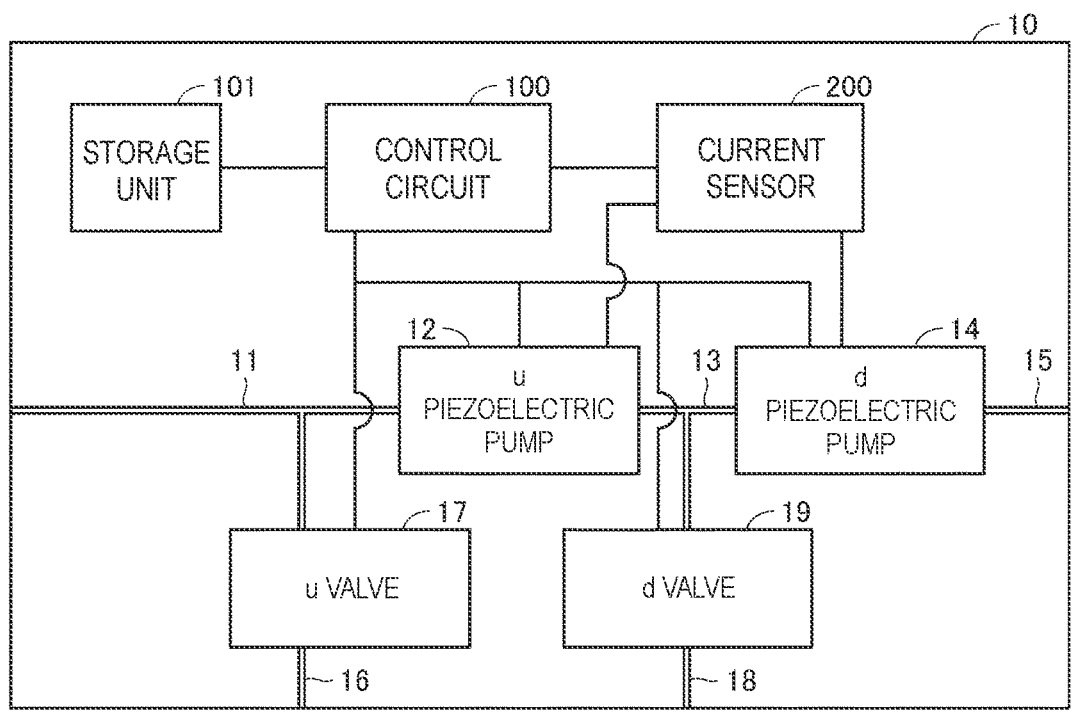
FIG. 3 is a block diagram describing the control of a pump unit according to an embodiment.
Each of FIGS. 4A and 4B is a diagram illustrating the relationship between a current difference between two pumps according to an embodiment and a back pressure.

Next, the pump unit 10 will be described in detail with reference to the drawings. FIG. 2 is a schematic diagram illustrating the configuration of the pump unit 10 according to an embodiment. FIG. 3 is a block diagram describing the control of the pump unit 10 according to an embodiment.

As illustrated in FIG. 2, the pump unit 10 includes a first flow path 11, a u piezoelectric pump 12 (first piezoelectric pump), a second flow path 13, a d piezoelectric pump 14 (second piezoelectric pump), and a third flow path 15. The first flow path 11 is provided on an upstream side for air intake. The u piezoelectric pump 12 has a first flow inlet and a first flow outlet, and one end of the first flow path 11 is connected to the first flow inlet. The second flow path 13 has one end connected to the first flow outlet of the u piezoelectric pump 12 and the other end connected to a second flow inlet of the d piezoelectric pump 14. The d piezoelectric pump 14 has the second flow inlet and a second flow outlet and is connected in series to the u piezoelectric pump 12. The third flow path 15 is connected to the second flow outlet of the d piezoelectric pump 14 and is provided on the downstream side.

The pump unit 10 in which the u piezoelectric pump 12 and the d piezoelectric pump 14 are connected in series can improve an output (a pressure will be hereinafter described by way of example). Even in the case where the u piezoelectric pump 12 and the d piezoelectric pump 14 are driven under the same conditions, more compressed air is delivered to the d piezoelectric pump 14 because the d piezoelectric pump 14 is located on the downstream side of the u piezoelectric pump 12. Since the back pressure at the d piezoelectric pump 14 is higher than that at the u piezoelectric pump 12, a current Id for driving the d piezoelectric pump 14 is lower than a current Iu for driving the u piezoelectric pump 12 to create a current difference in the case where the u piezoelectric pump 12 and the d piezoelectric pump 14 are driven at a constant voltage.

Since a current difference (Iu−Id) between the u piezoelectric pump 12 and the d piezoelectric pump 14 is determined in accordance with the difference in back pressure between the u piezoelectric pump 12 and the d piezoelectric pump 14, the current difference becomes constant when the u piezoelectric pump 12 and the d piezoelectric pump 14 have the same performance. However, the relationship between the current difference (Iu−Id) between the u piezoelectric pump 12 and the d piezoelectric pump 14 and a back pressure is not linear. Each of FIGS. 4A and 4B is a diagram illustrating the relationship between a current difference between two pumps according to an embodiment and a back pressure. As illustrated in FIGS. 4A and 4B, even if the difference in back pressure between the u piezoelectric pump 12 and the d piezoelectric pump 14 remains the same, the current difference (Iu−Id) between the u piezoelectric pump 12 and the d piezoelectric pump 14 changes in accordance with a sea level (atmospheric pressure) of a location where the u piezoelectric pump 12 and the d piezoelectric pump 14 are disposed.

Specifically, FIG. 4A illustrates the case where the u piezoelectric pump 12 and the d piezoelectric pump 14 are disposed at a low altitude of 0 m above sea level. When an atmospheric pressure at the location where the u piezoelectric pump 12 and the d piezoelectric pump 14 are disposed is high, back pressures themselves at the u piezoelectric pumps 12 and d piezoelectric pump 14 become high. As a result, even if the difference in back pressure between the u piezoelectric pump 12 and the d piezoelectric pump 14 remains the same, the current difference (Iu−Id) between the u piezoelectric pump 12 and the d piezoelectric pump 14 becomes small as illustrated in FIG. 4A.

On the other hand, FIG. 4B illustrates the case where the u piezoelectric pump 12 and the d piezoelectric pump 14 are disposed at a high altitude. When an atmospheric pressure at the location where the u piezoelectric pump 12 and the d piezoelectric pump 14 are disposed is low, back pressures themselves at the u piezoelectric pumps 12 and d piezoelectric pump 14 become low. As a result, even if the difference in back pressure between the u piezoelectric pump 12 and the d piezoelectric pump 14 remains the same, the current difference (Iu−Id) between the u piezoelectric pump 12 and the d piezoelectric pump 14 becomes large as illustrated in FIG. 4B.

In the pump unit 10, a pressure of at least one of the u piezoelectric pump 12 and the d piezoelectric pump 14 is adjusted on the basis of the current difference (Iu−Id) between the u piezoelectric pump 12 and the d piezoelectric pump 14 by using the relationships illustrated in FIGS. 4A and 4B. That is, in the case where the pump unit 10 is disposed at a high altitude, for example, the degrease in a back pressure is compensated for by increasing the pressures at the u piezoelectric pump 12 and the d piezoelectric pump 14. Alternatively, in the case where the pump unit 10 is disposed at a higher altitude, for example, a pressure at the u piezoelectric pump 12 is reduced to prevent a large current from flowing through the u piezoelectric pump 12.

By detecting an atmospheric pressure at the location where the pump unit 10 is disposed, at least one of the pressure of the u piezoelectric pump 12 and the pressure of the d piezoelectric pump 14 can be adjusted. However, a sensor such as a barometer needs to be added in this case. The addition of a sensor such as a barometer for the detection of an atmospheric pressure causes a demerit such as the increase in a manufacturing cost. In the present embodiment, a configuration will be described with which, even in the case where an atmospheric pressure changes, the pressures at the u piezoelectric pump 12 and the d piezoelectric pump 14 can be easily adjusted using the relationships illustrated in FIGS. 4A and 4B without the addition of a sensor such as a barometer.

The pump unit 10 also has a configuration for removing the contamination to eliminate a blockage state occurring in the flow path. Specifically, as illustrated in FIG. 2, the pump unit 10 further includes a first branch path 16 that is connected to the first flow path 11 and the outside of the flow path, a u valve 17 (first valve) disposed on the first branch path 16, a second branch path 18 that is connected to the second flow path 13 and the outside of the flow path, and a d valve 19 (second valve) disposed on the second branch path 18. The pump unit 10 does not necessarily have to have the configuration for removing the contamination.

As illustrated in FIG. 3, the pump unit 10 includes a control circuit 100 capable of controlling the driving of the u piezoelectric pump 12 and the d piezoelectric pump 14 and the opening/closing of the u valve 17 and the d valve 19, a storage unit 101, and a current sensor 200 (detection unit) for detecting the respective currents of the u piezoelectric pump 12 and the d piezoelectric pump 14. Although not illustrated, the nebulizer 1 includes a power supply for supplying the power required for the driving of the pump unit 10.

The control circuit 100 includes, for example, a CPU (central processing unit) functioning as a control center, a ROM (read-only memory) that stores, for example, programs or control data for operating the CPU, a RAM (random access memory) functioning as a work area for the CPU, and an input/output interface for maintaining the signal integrity with peripheral devices.

The storage unit 101 is a nonvolatile memory such as a flash memory or an SSD (solid state drive). The storage unit 101 stores a table indicating the relationship between the current difference (Iu−Id) between the u piezoelectric pump 12 and the d piezoelectric pump 14 and the pressure adjustment amounts for the u piezoelectric pump 12 and the d piezoelectric pump 14. FIG. 5 is a diagram illustrating the contents of a table stored in the storage unit 101 according to an embodiment. The table illustrated in FIG. 5 stores, for each sea level or atmospheric pressure, the current difference (Iu−Id) between the u piezoelectric pump 12 and the d piezoelectric pump 14 and the pressure adjustment amounts for the u piezoelectric pump 12 and the d piezoelectric pump 14. The storage unit 101 may store the relationship between the current difference (Iu−Id) between the u piezoelectric pump 12 and the d piezoelectric pump 14 and the pressure adjustment amounts for the u piezoelectric pump 12 and the d piezoelectric pump 14 in the form of a function instead of in the form of a table illustrated in FIG. 5.

When activated, the pump unit 10 compresses, in the u piezoelectric pump 12 and the d piezoelectric pump 14, the air sucked from the upstream side (left side in the drawing) of the first flow path 11 and delivers the compressed air from the downstream side (right side in the drawing) of the third flow path 15 to the air nozzle 20. Accordingly, the control circuit 100 drives the u piezoelectric pump 12 and the d piezoelectric pump 14 in predetermined driving conditions for the flow of a fluid from the upstream side of the first flow path 11 to the downstream side of the third flow path 15. For example, the control circuit 100 drives the u piezoelectric pump 12 and the d piezoelectric pump 14 at a constant voltage. In particular, if there is no need to differentiate the driving conditions for the u piezoelectric pump 12 and the d piezoelectric pump 14, the u piezoelectric pump 12 and the d piezoelectric pump 14 are driven at the same constant voltage.

The driving conditions for the u piezoelectric pump 12 and the d piezoelectric pump 14 are not limited to the conditions for driving at a constant voltage and may be other driving conditions for driving at a constant current. The driving conditions for the u piezoelectric pump 12 and driving conditions for the d piezoelectric pump 14 do not necessarily have to be the same and may differ from each other such that, for example, the workload of the d piezoelectric pump 14 on the downstream side is higher than that of the u piezoelectric pump 12 on the upstream side. In the case where these driving conditions are made to differ from each other, the u piezoelectric pump 12 and the d piezoelectric pump 14 need to be driven in a range in which the current Iu of the u piezoelectric pump 12 is higher than the current Id of the d piezoelectric pump 14.

The control circuit 100 detects the current Iu of the u piezoelectric pump 12 and the current Id of the d piezoelectric pump 14 using the current sensor 200 to obtain the current difference (Iu−Id) between the u piezoelectric pump 12 and the d piezoelectric pump 14. However, the current difference between the u piezoelectric pump 12 and the d piezoelectric pump 14 may be directly detected using, for example, an OP amplifier. In the case where the control circuit 100 drives the u piezoelectric pump 12 and the d piezoelectric pump 14 at a constant current, a voltage sensor may be disposed instead of the current sensor 200 and may detect a voltage Vu of the u piezoelectric pump 12 and a voltage Vd of the d piezoelectric pump 14 and obtain a voltage difference (Vu−Vd) between the u piezoelectric pump 12 and the d piezoelectric pump 14. The control circuit 100 may adjust at least one of a pressure at the u piezoelectric pump 12 and a pressure at the d piezoelectric pump 14 on the basis of the voltage difference (Vu−Vd) between the u piezoelectric pump 12 and the d piezoelectric pump 14. The control circuit 100 may adjust at least one of a pressure at the u piezoelectric pump 12 and a pressure at the d piezoelectric pump 14 on the basis of a power difference (Wu−Wd) between power Wu of the u piezoelectric pump 12 and power Wd of the d piezoelectric pump 14.

Figure 6:
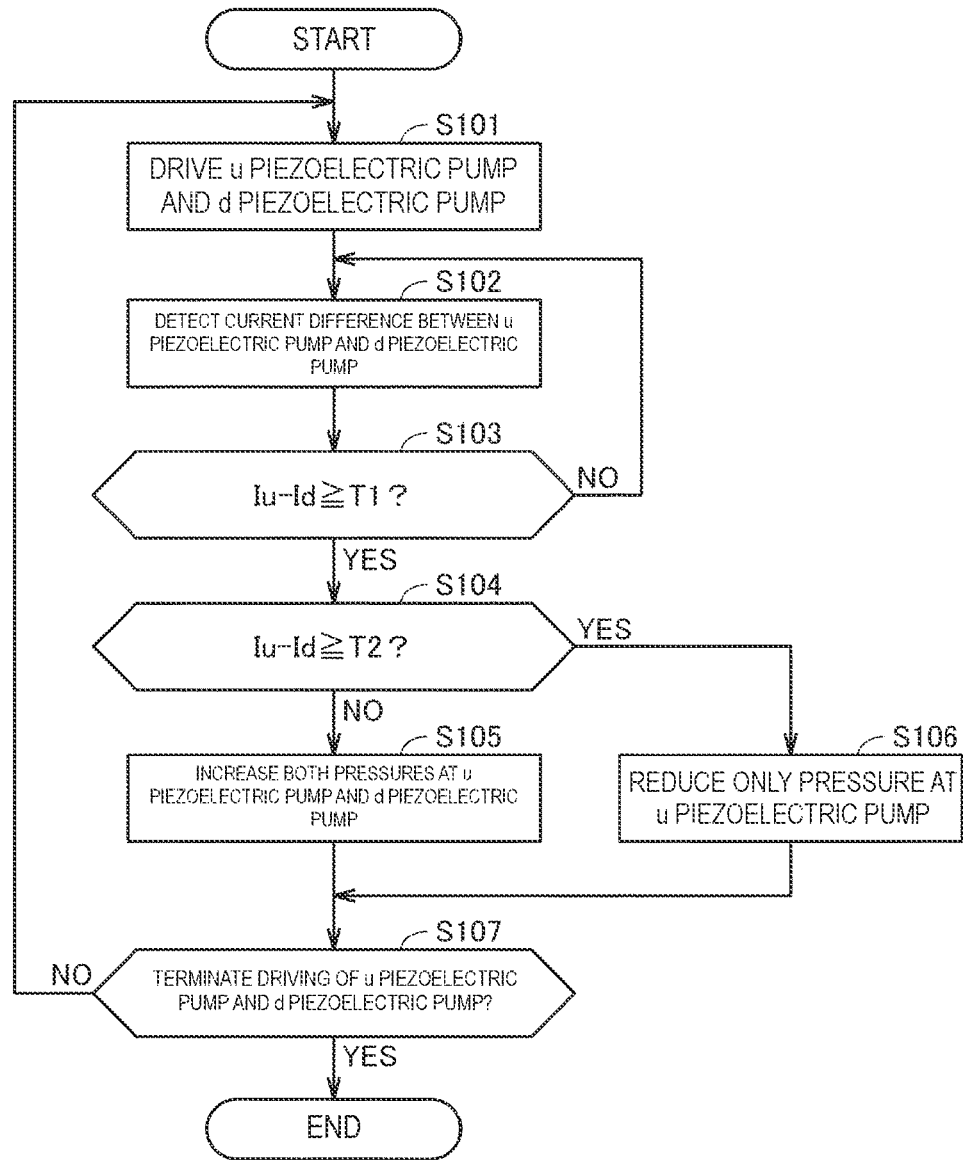
FIG. 6 is a flowchart describing the operation of a pump unit according to an embodiment.

Next, an operation of adjusting the u piezoelectric pump 12 and the d piezoelectric pump 14 in the pump unit 10 will be described with reference to a flowchart. FIG. 6 is a flowchart describing the operation of the pump unit 10 according to an embodiment. First, when the pump unit 10 is activated, the control circuit 100 drives the u piezoelectric pump 12 and the d piezoelectric pump 14 in predetermined driving conditions (step S101).

The control circuit 100 obtains the current difference (Iu−Id) between the u piezoelectric pump 12 and the d piezoelectric pump 14 in a state in which the u piezoelectric pump 12 and the d piezoelectric pump 14 are driven in the predetermined driving conditions (step S102). The current Iu of the u piezoelectric pump 12 and the current Id of the d piezoelectric pump 14 are detected by the current sensor 200 and are inputted to the control circuit 100. The control circuit 100 calculates the current difference (Iu−Id) between the u piezoelectric pump 12 and the d piezoelectric pump 14 from the current Iu of the u piezoelectric pump 12 and the current Id of the d piezoelectric pump 14 detected by the current sensor 200.

The control circuit 100 determines whether the detected current difference (Iu−Id) between the u piezoelectric pump 12 and the d piezoelectric pump 14 is greater than or equal to a threshold value T1 (step S103). As illustrated in FIG. 5, the table indicates that the respective pressures at the u piezoelectric pump 12 and the d piezoelectric pump 14 are increased by 20% for the compensation for the decrease in a back pressure at 1000 m or higher above sea level. Accordingly, the control circuit 100 can determine whether the location where the u piezoelectric pump 12 and the d piezoelectric pump 14 are disposed is at a high altitude of 1000 m or higher above sea level and adjust the respective pressures at the u piezoelectric pump 12 and the d piezoelectric pump 14 by determining whether the current difference (Iu−Id) between the u piezoelectric pump 12 and the d piezoelectric pump 14 is greater than or equal to β (=the threshold value T1).

In the case where the control circuit 100 determines that the current difference (Iu−Id) between the u piezoelectric pump 12 and the d piezoelectric pump 14 is less than the threshold value T1 (NO in step S103), the control circuit 100 determines that there is no need to adjust the respective pressures at the u piezoelectric pump 12 and the d piezoelectric pump 14 and returns the process to S102. That is, the control circuit 100 continues to obtain the current difference (Iu−Id) between the u piezoelectric pump 12 and the d piezoelectric pump 14 while continuing the driving of the u piezoelectric pump 12 and the d piezoelectric pump 14 in the predetermined driving conditions.

On the other hand, in the case where the control circuit 100 determines that the detected current difference (Iu−Id) between the u piezoelectric pump 12 and the d piezoelectric pump 14 is greater than or equal to the threshold value T1 (YES in step S103), the control circuit 100 determines whether the detected current difference (Iu−Id) between the u piezoelectric pump 12 and the d piezoelectric pump 14 is greater than or equal to a threshold value T2 (step S104). As illustrated in FIG. 5, the table indicates that, at 3000 m or higher above sea level, only the pressure at the u piezoelectric pump 12 is reduced by 30% to protect the u piezoelectric pump 12 when a larger current flows through the u piezoelectric pump 12. Accordingly, the control circuit 100 can determine whether the location where the u piezoelectric pump 12 and the d piezoelectric pump 14 are disposed is at a high altitude of 3000 m or higher above sea level and adjust the pressure at the u piezoelectric pump 12 by determining whether the current difference (Iu−Id) between the u piezoelectric pump 12 and the d piezoelectric pump 14 is greater than or equal to δ (=the threshold value T2).

In the case where the control circuit 100 determines that the current difference (Iu−Id) between the u piezoelectric pump 12 and the d piezoelectric pump 14 is less than the threshold value T2 (NO in step S104), the control circuit 100 increases both the pressure at the u piezoelectric pump 12 and the pressure at the d piezoelectric pump 14 (step S105). Specifically, the control circuit 100 increases the respective pressures at the u piezoelectric pump 12 and the d piezoelectric pump 14 by 20% as indicated by the table illustrated in FIG. 5. The control circuit 100 can adjust the respective pressures at the u piezoelectric pump 12 and the d piezoelectric pump 14 by changing at least one of a current, a frequency, and a voltage for driving the u piezoelectric pump 12 and the d piezoelectric pump 14.

On the other hand, in the case where the control circuit 100 determines that the current difference (Iu−Id) between the u piezoelectric pump 12 and the d piezoelectric pump 14 is greater than or equal to the threshold value T2 (YES in step S104), the control circuit 100 reduces only the pressure at the u piezoelectric pump 12 (step S106). Specifically, the control circuit 100 reduces only the pressure at the u piezoelectric pump 12 by 30% as indicated by the table illustrated in FIG. 5. In the case where the control circuit 100 determines that the current difference (Iu−Id) between the u piezoelectric pump 12 and the d piezoelectric pump 14 is greater than or equal to the threshold value T2 (YES in step S104), the control circuit 100 may reduce the pressure at the u piezoelectric pump 12 more than the pressure at the d piezoelectric pump 14 while reducing the pressure at the d piezoelectric pump 14.

Subsequently, the control circuit 100 continues the driving of the u piezoelectric pump 12 and the d piezoelectric pump 14 in the predetermined driving conditions and determines whether an input for the termination of the driving of the u piezoelectric pump 12 and the d piezoelectric pump 14 has been received from a user (for example, the patient P) (step S107).

In the case where an input for the termination of the driving of the u piezoelectric pump 12 and the d piezoelectric pump 14 has not been received from a user (NO in step S107), the control circuit 100 returns the process to the S102. That is, the control circuit 100 continues to cause the current sensor 200 to detect the current Iu of the u piezoelectric pump 12 and the current Id of the d piezoelectric pump 14 while continuing the driving of the u piezoelectric pump 12 and the d piezoelectric pump 14 in the predetermined driving conditions.

On the other hand, in the case where an input for the termination of the driving of the u piezoelectric pump 12 and the d piezoelectric pump 14 has been received from a user (YES in step S107), the control circuit 100 terminates the driving of the u piezoelectric pump 12 and the d piezoelectric pump 14 and ends the process.

As described above, the pump unit 10 according to an embodiment includes the first flow path 11, the u piezoelectric pump 12 having a first flow inlet connected to one end of the first flow path 11 and a first flow outlet, the d piezoelectric pump 14 having a second flow inlet and a second flow outlet, the second flow path 13 having one end connected to the first flow outlet of the u piezoelectric pump 12 and another end connected to the second flow inlet of the d piezoelectric pump 14, the third flow path 15 connected to the second flow outlet of the d piezoelectric pump 14, the control circuit 100 capable of controlling driving of the u piezoelectric pump 12 and the d piezoelectric pump 14, and the current sensor 200 configured to detect a current of the u piezoelectric pump 12 and a current of the d piezoelectric pump 14. The control circuit 100 is capable of adjusting at least one of an output (e.g., a pressure or a flowrate) of the u piezoelectric pump 12 and an output of the d piezoelectric pump 14 based on the difference (Iu−Id) between the current Iu of the u piezoelectric pump 12 and the current Id of the d piezoelectric pump 14 detected by the current sensor 200.

The pump unit 10 according to an embodiment adjusts at least one of the output of the u piezoelectric pump 12 and the output of the d piezoelectric pump 14 on the basis of the detected difference (Iu−Id) between the current Iu of the u piezoelectric pump 12 and the current Id of the d piezoelectric pump 14. Accordingly, even if an atmospheric pressure changes, the output of a pump can be easily adjusted.

The pump unit 10 further includes the storage unit 101 storing in advance a table indicating a relationship between the difference (Iu−Id) between the current Iu of the u piezoelectric pump 12 and the current Id of the d piezoelectric pump 14 and output adjustment amounts for the u piezoelectric pump 12 and the d piezoelectric pump 14. It is desired that the control circuit 100 be capable of reading from the table output adjustment amounts for the u piezoelectric pump 12 and the d piezoelectric pump 14 corresponding to the difference (Iu−Id) between the current Iu of the u piezoelectric pump 12 and the current Id of the d piezoelectric pump 14 detected by the current sensor 200 and adjusting at least one of the output of the u piezoelectric pump 12 and the output of the d piezoelectric pump 14 using the output adjustment amounts. As a result, the pump unit 10 can easily adjust at least one of the output of the u piezoelectric pump 12 and the output of the d piezoelectric pump 14 using the table.

It is desired that the table store in advance a relationship between an atmospheric pressure or a height of a location where u piezoelectric pump 12 and d piezoelectric pump 14 are disposed and the difference (Iu−Id) between the current Iu of the u piezoelectric pump 12 and the current Id of the d piezoelectric pump 14. As a result, the pump unit 10 can specify the atmospheric pressure or height of the location where the u piezoelectric pump 12 and the d piezoelectric pump 14 are disposed from the difference (Iu−Id) between the current Iu of the u piezoelectric pump 12 and the current Id of the d piezoelectric pump 14.

When the difference (Iu−Id) between the current Iu of the u piezoelectric pump 12 and the current Id of the d piezoelectric pump 14 detected by the current sensor 200 exceeds the threshold value T1 (a first threshold value) set in advance for the table, it is desired that the control circuit 100 be capable of performing adjustment such that both the output of the u piezoelectric pump 12 and the output of the d piezoelectric pump 14 increase. As a result, the pump unit 10 can compensate for the decrease in a back pressure caused by the decrease in the atmospheric pressure of the location where the u piezoelectric pump 12 and the d piezoelectric pump 14 are disposed.

When the difference (Iu−Id) in electric quantity between the current Iu of the u piezoelectric pump 12 and the current Id of the d piezoelectric pump 14 detected by the current sensor 200 exceeds a second threshold value greater than the first threshold value, it is desired that the control circuit 100 be capable of performing adjustment such that only the output of the u piezoelectric pump 12 decreases. As a result, the pump unit 10 can prevent the flow of a large current through the u piezoelectric pump 12 and protect the u piezoelectric pump 12.

Instead of the current sensor 200 for detecting a current, a detection unit for detecting a voltage or power may be used. In the present disclosure, a current, a voltage, and power are collectively called electric quantity.

It is desired that the control circuit 100 be capable of adjusting the output of the u piezoelectric pump 12 and the output of the d piezoelectric pump 14 by changing at least one of a current, a frequency, and a voltage for driving the u piezoelectric pump 12 and the d piezoelectric pump 14.

An output adjustment method of adjusting the output of the u piezoelectric pump 12 and the output of the d piezoelectric pump 14 in the pump unit 10 includes a step of detecting the difference (Iu−Id) between the current Iu of the u piezoelectric pump 12 and the current Id of the d piezoelectric pump 14 and a step of adjusting at least one of the output of the u piezoelectric pump 12 and the output of the d piezoelectric pump 14 on the basis of the detected difference (Iu−Id) between the current Iu of the u piezoelectric pump 12 and the current Id of the d piezoelectric pump 14.

In an output adjustment method of the pump unit 10 according to an embodiment, at least one of the output of the u piezoelectric pump 12 and the output of the d piezoelectric pump 14 is adjusted on the basis of the difference (Iu−Id) between the current Iu of the u piezoelectric pump 12 and the current Id of the d piezoelectric pump 14. Accordingly, even if an atmospheric pressure changes, the output of the pump can be easily adjusted.

(Other Modifications)

Figure 7:
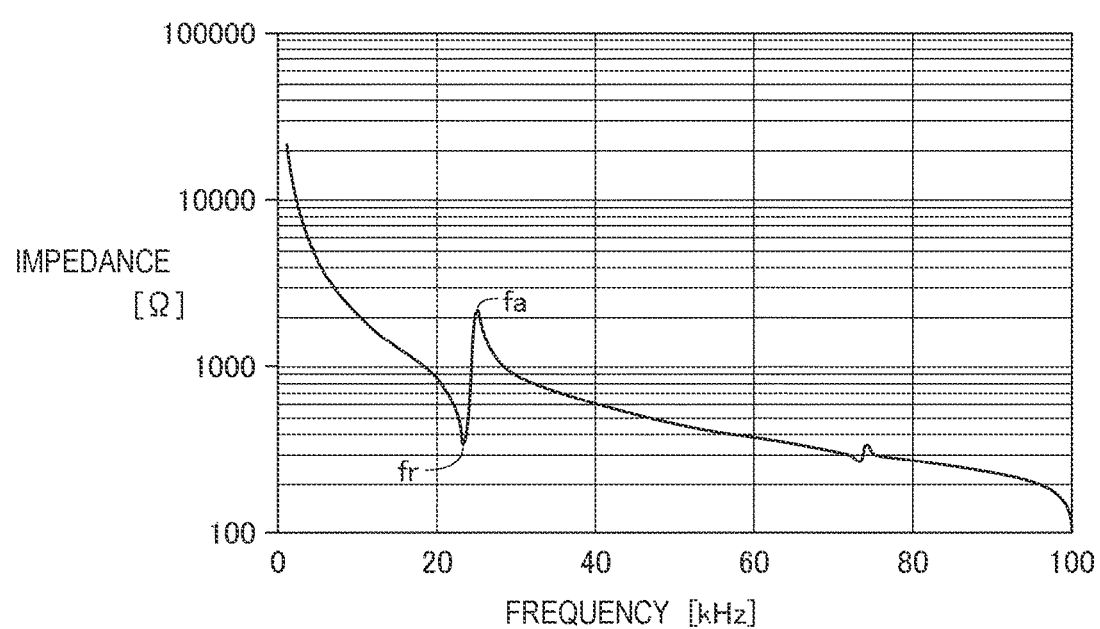
FIG. 7 is a diagram illustrating the relationship between the frequency of a piezoelectric pump according to an embodiment and an impedance.

In the pump unit 10 according to an embodiment described above, a frequency for driving the u piezoelectric pump 12 and the d piezoelectric pump 14 is adjusted for the adjustment of the respective pressures at the u piezoelectric pump 12 and the d piezoelectric pump 14. This will be further described in detail with reference to the frequency characteristics of the u piezoelectric pump 12 and the d piezoelectric pump 14. FIG. 7 is a diagram illustrating the relationship between the frequency of a pump according to an embodiment and an impedance. Referring to FIG. 7, a graph represents the relationship between the frequency of a piezoelectric pump and an impedance at ordinary temperatures (e.g., 20° C.).

The frequency characteristics of the u piezoelectric pump 12 and the d piezoelectric pump 14 have a resonant frequency fr and an anti-resonant frequency fa. The resonant frequency fr is approximately 23.4 kHz, and the anti-resonant frequency fa is approximately 24.5 kHz. Between the resonant frequency fr and the anti-resonant frequency fa, a piezoelectric pump can be driven.

In the case where the u piezoelectric pump 12 and the d piezoelectric pump 14 include respective self-excitation circuits, the control circuit 100 generally drives the u piezoelectric pump 12 and the d piezoelectric pump 14 at the resonant frequency fr. However, when adjusting the respective pressures at the u piezoelectric pump 12 and the d piezoelectric pump 14, the control circuit 100 turns off the self-excitation circuits and drives the u piezoelectric pump 12 and the d piezoelectric pump 14 at a frequency shifted from the resonant frequency fr.

In the case where the u piezoelectric pump 12 and the d piezoelectric pump 14 are driven by separate excitation, the control circuit 100 drives the u piezoelectric pump 12 and the d piezoelectric pump 14 at a driving frequency set in advance. However, when adjusting the respective pressures at the u piezoelectric pump 12 and the d piezoelectric pump 14, the control circuit 100 drives the u piezoelectric pump 12 and the d piezoelectric pump 14 at a frequency shifted from the driving frequency set in advance.

As described above, the table illustrated in FIG. 5 is stored in advance in the storage unit 101 in the pump unit according to an embodiment. The timing of the storage of the table in the storage unit 101 may be at the time of manufacture in a factory or at the time of use by a user. The table stored in the storage unit 101 can be changed or corrected by a user. For example, a user may input a sea level (or an atmospheric pressure) as an initial setting when using the pump unit 10, and the control circuit 100 may correct values in the table stored in the storage unit 101 on the basis of information about the input sea level (or an input atmospheric pressure).

The pump unit 10 or a device using the pump unit 10 (e.g., the nebulizer 1) may include a display. The pump unit may display on the display information about the sea level or atmospheric pressure of the location where the u piezoelectric pump 12 and the d piezoelectric pump 14 are disposed which is determined on the basis of the difference (Iu−Id) between the current Iu of the u piezoelectric pump 12 and the current Id of the d piezoelectric pump 14.

The embodiment disclosed herein is illustrative only and is not intended to be limiting in any way. The scope of the present disclosure is defined by the appended claims rather than the foregoing description, and it should be understood that all the changes conceived from the meaning and scope of the claims and their equivalents are included in the scope of the present disclosure.

1 nebulizer
10 pump unit
11 first flow path
12 and 14 piezoelectric pump 13 second flow path
15 third flow path
16 first branch path
17 and 19 valve
18 second branch path
20 air nozzle
30 atomizing nozzle
40 drug solution tank
42 pipe
50 mouthpiece
100 control circuit
101 storage unit
200 current sensor

The invention claimed is:

1. A fluid control device comprising:
a first flow path;
a first pump having a first flow inlet connected to a first end of the first flow path and to a first flow outlet;
a second pump having a second flow inlet and a second flow outlet;
a second flow path having a first end connected to the first flow outlet of the first pump, and a second end connected to the second flow inlet of the second pump;
a third flow path connected to the second flow outlet of the second pump;
a controller configured to drive the first pump and the second pump;
a sensor configured to detect an electric quantity of the first pump and an electric quantity of the second pump; and
storage configured to store a table indicating a relationship between the difference between the detected electric quantities of the first pump and the second pump, and output adjustment amounts for the first pump and the second pump,
wherein the controller is configured to adjust at least one of an output of the first pump or an output of the second pump based on a difference between the detected electric quantities of the first pump and the second pump,
wherein the controller is configured to read from the table the output adjustment amounts for the first pump and the second pump corresponding to the difference between the detected electric quantities of the first pump and the second pump, and to adjust at least one of the output of the first pump or the output of the second pump based on the output adjustment amounts,
wherein when the difference between the detected electric quantities of the first pump and the second pump exceeds a first threshold value, the controller is configured to perform adjustment such that both the output of the first pump and the output of the second pump increase, and
wherein when the difference between the detected electric quantities of the first pump and the second pump exceeds a second threshold value greater than the first threshold value, the controller is configured to perform adjustment such that only the output of the first pump decreases.

2. The fluid control device according to claim 1, wherein the table indicates a relationship between an atmospheric pressure or a height of a location where the first pump and the second pump are disposed, and the difference between the detected electric quantities of the first pump and the second pump.

3. The fluid control device according to claim 1, wherein the detected electric quantity is a value of a voltage, a current, or a power.

4. The fluid control device according to claim 1, wherein the controller is configured to adjust the output of the first pump and the output of the second pump by changing at least one of a current, a frequency, or a voltage for driving the first pump or the second pump.

5. An output adjustment method of adjusting at least one of an output of a first pump or an output of a second pump in a fluid control device that comprises a first flow path, the first pump having a first flow inlet connected to a first end of the first flow path and to a first flow outlet, the second pump having a second flow inlet and a second flow outlet, a second flow path having a first end connected to the first flow outlet of the first pump and a second end connected to the second flow inlet of the second pump, a third flow path connected to the second flow outlet of the second pump, a controller configured to drive the first pump and the second pump, and a sensor, the output adjustment method comprising:
detecting, with the sensor, an electric quantity of the first pump and an electric quantity of the second pump; and
adjusting, by the controller, at least one of the output of the first pump or the output of the second pump based on a difference between the detect electric quantities of the first pump and the second pump such that only the output of the first pump decreases,
wherein the difference between the detected electric quantities of the first pump and the second pump exceeds a second threshold value, and
wherein the second threshold value is greater than a first threshold value at which the controller is configured to adjust at least one of the output of the first pump or the output of the second pump such that both the output of the first pump and the output of the second pump increase.

6. The output adjustment method according to claim 5, comprising adjusting at least one of the output of the first pump or the output of the second pump such that both the output of the first pump and the output of the second pump increase,
wherein the difference between the detected electric quantities of the first pump and the second pump exceeds a first threshold value.

7. The output adjustment method according to claim 5, wherein the detected electric quantity is a value of a voltage, a current, or a power.

8. The output adjustment method according to claim 5, wherein adjusting at least one of the output of the first pump or the output of the second pump comprises changing at least one of a current, a frequency, or a voltage for driving the first pump or the second pump.

* * * * *